US008066876B2

(12) United States Patent
Hampton et al.

(10) Patent No.: US 8,066,876 B2
(45) Date of Patent: Nov. 29, 2011

(54) APPARATUS AND METHODS FOR PACKING CHROMATOGRAPHY COLUMNS

(75) Inventors: Thomas Wesley Hampton, Narragansett, RI (US); Nigel Green, Church Stretton (DE)

(73) Assignee: Agilent Technologies, Inc., Santa Clara, CA (US)

( * ) Notice: Subject to any disclaimer, the term of this patent is extended or adjusted under 35 U.S.C. 154(b) by 3 days.

(21) Appl. No.: 12/623,771

(22) Filed: Nov. 23, 2009

(65) Prior Publication Data

US 2011/0120951 A1    May 26, 2011

(51) Int. Cl.
*B01D 15/08* (2006.01)
(52) U.S. Cl. .................................. 210/198.2; 210/656
(58) Field of Classification Search ............... 210/198.2, 210/635, 656, 659; 95/82; 96/101
See application file for complete search history.

(56) References Cited

U.S. PATENT DOCUMENTS

| | | | |
|---|---|---|---|
| 4,582,608 A | | 4/1986 | Ritacco |
| 4,737,292 A | | 4/1988 | Ritacco et al. |
| 5,192,433 A | | 3/1993 | Shalon |
| 5,366,621 A | * | 11/1994 | Bidell et al. ............... 210/198.2 |
| 5,893,971 A | | 4/1999 | Shalon et al. |
| 5,951,873 A | | 9/1999 | Shalon et al. |
| 6,001,260 A | | 12/1999 | Hatch et al. |
| 6,036,855 A | | 3/2000 | Shalon et al. |
| 6,736,974 B1 | * | 5/2004 | Mann ............................. 210/656 |
| 7,686,953 B2 | * | 3/2010 | Bailey et al. ................ 210/198.2 |
| 7,708,891 B2 | * | 5/2010 | Davis et al. .................... 210/656 |
| 7,780,853 B2 | * | 8/2010 | Davis et al. .................... 210/656 |
| 7,785,473 B2 | * | 8/2010 | Davis et al. .................... 210/656 |
| 2009/0039008 A1 | | 2/2009 | Davis et al. |

FOREIGN PATENT DOCUMENTS

| | | |
|---|---|---|
| FR | 2 898 064 A1 | 9/2007 |
| WO | WO 97/32207 | 9/1997 |
| WO | 2005056156 A1 | 6/2005 |
| WO | WO 2007/045491 A2 | 4/2007 |
| WO | 2008076830 A2 | 6/2008 |
| WO | WO 2009/105216 A2 | 8/2009 |

OTHER PUBLICATIONS

"Spring(TM) Column Hardware", www.discoverysciences.com, pp. 162-165.
"Multipacker(R) Packing Stations", www.discoverysciences.com, pp. 172-173.
"MODcol(R) Spring (R) Columns and MultiPacker(R) Instruments", Grace Davison Discovery Sciences, www.discoverysciences.com, Technical Note, May 2009, 5pgs.
HPLC "Load & Lock(TM)", Varian, Inc. Columns and Packing Station, www.varianinc.com, pp. 1-8.

(Continued)

*Primary Examiner* — Ernest G Therkorn

(57) ABSTRACT

A chromatographic apparatus may include a hydraulic lifting mechanism axially movable from a lowered position to a raised position such that a column and flange of the apparatus are axially movable with the hydraulic lifting mechanism. In a packing system, a mobile column module may be moved into engagement with a packing station by engaging a flange of the column module with a fixture of the packing station. After packing a column of the column module, the column module may be removed from the packing station with a piston head locked in the column to maintain packing pressure. The packing station may be utilized to unpack the column. A hydraulic lifting mechanism may be operated to lower one or more portions of the column module such that the one or more portions may be separately removed from the packing system.

14 Claims, 11 Drawing Sheets

OTHER PUBLICATIONS

Bayer Technology Services, "Process Chromatography", info@bayertechnology.com, Dec. 2004, pp. 1-8.

Partial EPO Search Report from Corresponding European Patent Application No. 10014804.8-2113, 5 pgs. (Feb. 22, 2011).

Extended EPO Search Report from Corresponding European Patent Application No. 10014804.8-2113, 11 pgs. (Jun. 8, 2011).

Abstract of Japan Patent No. 63-134952.

* cited by examiner

APPARATUS AND METHODS FOR PACKING CHROMATOGRAPHY COLUMNS

FIELD OF THE INVENTION

The present invention relates generally to chromatography columns and column packing systems.

BACKGROUND OF THE INVENTION

Liquid chromatography (LC) is a technique for performing an analytical separation or a preparative separation of a liquid-phase material of interest (e.g., a mixture of different chemical compounds) into constituent components. During the course of a chromatographic separation, the material of interest is transported in a mobile phase (or solvent). The mobile phase is forced through a stationary phase that is immiscible relative to the mobile phase. Typically, the stationary phase is provided in the form of a volume of particles (a column packing bed) supported in a column through which the material to be separated and the mobile phase flow. The column packing bed is typically retained at each end of the column by a frit or filter that allows the mobile phase and the material to be separated to flow through while preventing the packing material from escaping the column. In the column, the respective compositions of the mobile phase and stationary phase are selected to cause differing components of the material of interest to become distributed between the mobile phase and stationary phase to varying degrees dependent on the respective chemistries of the material's components. Components that are strongly retained by the stationary phase travel slowly with the mobile phase, while components that are weakly retained by the stationary phase travel more rapidly. As a result, components of differing compositions become separated from each other as the mobile phase flows through the column.

In analytical separation, the components are separated to facilitate their analysis by known detecting techniques. Analytical separation typically entails the use of a small amount of material and small inside-diameter columns (e.g, less than 1 inch). In preparative separation, the components are separated to purify or isolate one or more chemical components from the starting material, which may be done for a further use such as reaction, synthesis, etc. Preparative separation is typically performed on a much larger scale to purify a large quantity of material, and hence typically utilizes large inside-diameter columns (e.g., 1-24 inches).

The packing and handling of large columns have conventionally required the use of large, heavy equipment. Large columns are typically packed by a flow packing technique, which entails suspending the particulate packing material in a suitable solvent to form a slurry, forcing the slurry into the column to retain the packing material while allowing the solvent to pass through the column, and then rapidly compressing the packing material by axial compression to form a uniform, tightly-packed bed at a desired final pressure. Axial compression is typically accomplished by driving a piston head through the column and into contact with the packing material. Axial compression and handling of columns is typically done pneumatically, which may not be sufficiently robust for larger-scale columns. Moreover, axial compression typically requires a column to be loaded into a column packing station. The packing station is often stationary or at least too heavy or bulky to be transported easily, and the column is often too large or heavy to be handled easily. Consequently, the packing station is often required to be located directly at the site of operation of the column, i.e., the location where the column is utilized to perform separation. Thus, there is a risk that fluids or other components of the packing station may contaminate the column, and the packing station may not be available to pack other columns while the packed column is being utilized in a separation process. Moreover, the typical packing station is compatible for use with only one or a few different column sizes, and is limited to a narrow range of packing pressures.

In view of the foregoing, there is a need for providing chromatographic column hardware configured for easier and more robust handling and packing of columns of differing sizes, including large-scale columns, and over a wide range of selectable packing pressures and packing material compositions. There is also a need for improving the mobility of columns to enable a packed column to be easily transported to a site of operation located remotely from the packing station, so as to isolate the separation process from the packing/unpacking process and prevent decompression of the packed column. There is also a need for reducing the bulk and weight of the apparatus utilized for handling and transporting a packed column.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a chromatographic apparatus includes a frame, a column removably supported by the frame and comprising a first end and an axially opposing second end, a piston head axially movable in the column and removable from the column, a flange attached to the frame in a fixed position at an axial distance from the first end, a rod extending through a bore of the flange and removably coupled to the piston head, a locking mechanism, and a hydraulic lifting mechanism communicating with the frame. The locking mechanism is movable from an unlocked state in which the rod and the piston head are axially movable, to a locked state in which the locking mechanism prevents the rod and the piston head from axially moving away from the column. The hydraulic lifting mechanism is axially movable from a lowered position to a raised position, wherein the column and the flange are axially movable with the hydraulic lifting mechanism.

According to another implementation, a chromatographic packing system includes a first frame, a hydraulic compression mechanism, a second frame, a column, a piston head, a piston rod, and a locking mechanism. The first frame includes a mounting fixture. The hydraulic compression mechanism is supported by the first frame and includes a coupling axially movable from a raised position to a lowered position. The second frame includes a flange removably engaged with the mounting fixture. The column is supported by the second frame and includes a first end located at an axial distance from the flange and an axially opposing second end. The piston head is axially movable in the column and removable from the column. The piston rod is removably coupled to the piston head and removably coupled to the coupling, wherein the piston rod and the piston head are axially movable with the coupling. The locking mechanism is movable from an unlocked state in which the piston rod and the piston head are axially movable, to a locked state in which the locking mechanism prevents the piston rod and the piston head from axially moving away from the column. The second frame, the column, the piston head and the piston rod are removably mounted as a unit to the mounting fixture via the engagement of the flange.

According to another implementation, a method is provided for operating a chromatographic packing system. A mobile column module is moved into engagement with a packing station by mounting a flange of the mobile column module in a mounting fixture of the packing station. The mobile column module includes a column, a piston rod, a piston head removably coupled to the piston rod, and a mobile frame supporting the column. The piston rod is coupled to a hydraulic compression mechanism of the packing station. The hydraulic compression mechanism is operated to drive the piston head into the column. One or more portions of the mobile column module are detached from the packing station by moving the mobile frame away from the packing station with the one or more portions supported by the mobile frame, wherein the one or more portions are selected from the group consisting of a column end cap, the column end cap and the column, and the entire mobile column module.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

Figure 1:
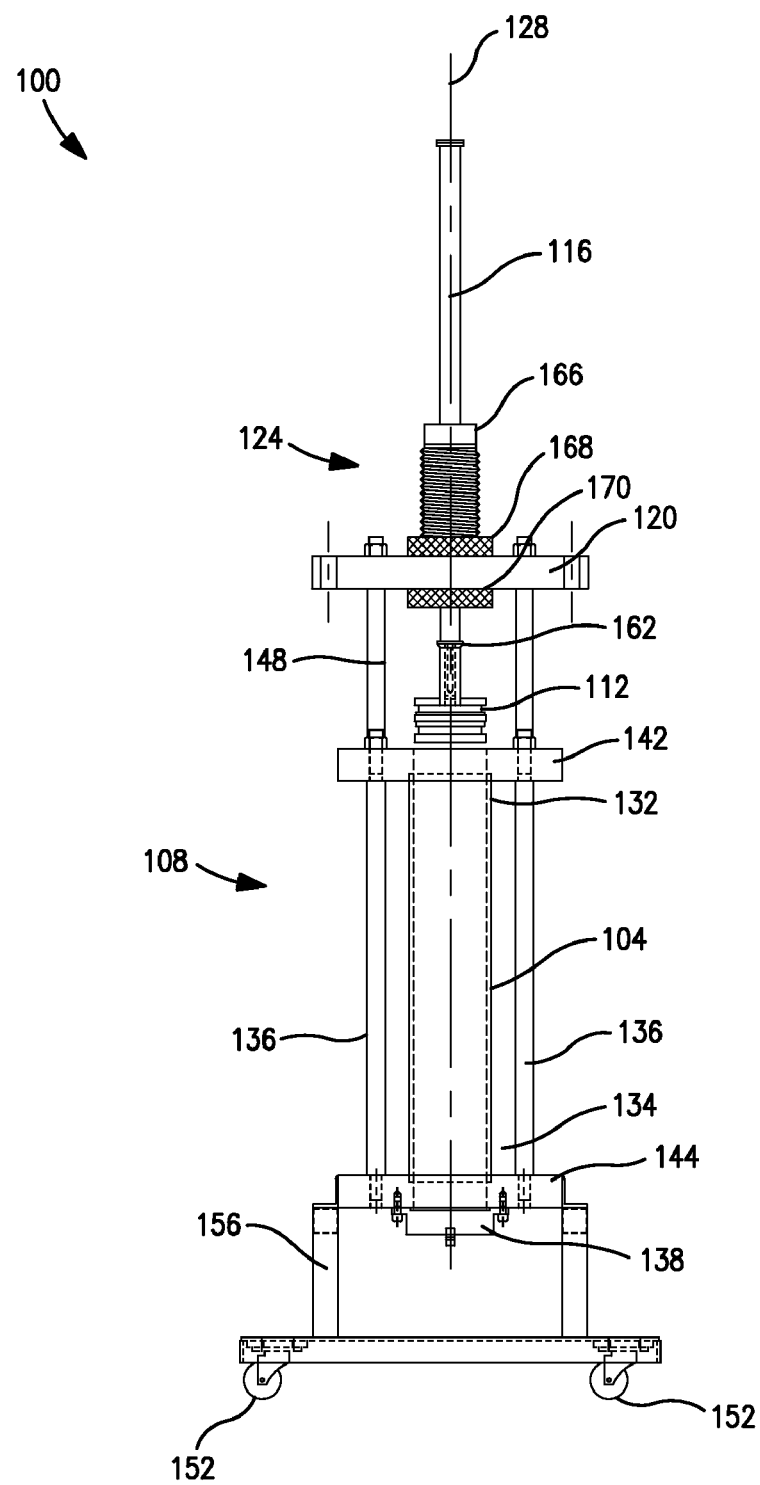
FIG. 1 is an elevation view of an example of a chromatography column module (or assembly) according to an implementation of the present disclosure.

FIG. 1 is an elevation view of an example of a chromatography column module (or assembly) 100 according to an implementation of the present disclosure. The column module 100 generally includes a chromatography column 104 supported by a frame 108, a piston (or compression) head 112, a piston (or compression) rod 116, a compression flange (or plate, etc.) 120, and a locking mechanism 124. The column 104 is generally oriented along a longitudinal axis 128 that in typical modes of operation is a vertical axis. The column 104 generally includes a first end 132 and an axially opposing second end 134. The first end 132 and the second end 134 may be initially open to the interior of the column 104. The piston head 112 may be located at the first end 132 to provide an upper boundary of the column interior, and an end cap 138 may be located at the second end 134 to provide a lower boundary of the column interior. As appreciated by persons skilled in the art, the piston head 112 typically includes a porous frit or filter (not shown), and one or more fluid passages and/or fluid distribution structures (not shown) configured for defining an inlet fluid path from outside the column 104, through the frit, and into the column interior. Likewise, the end cap 138 typically includes a porous frit or filter (not shown), and one or more fluid passages and/or fluid distribution structures (not shown) configured for defining an outlet fluid path from the column interior, through the fit, and out from the end cap 138. The piston head 112 and the end cap 138 each may include one or more fluid seals (not shown) as needed. As appreciated by persons skilled in the art, the respective fits of the movable piston head 112 and the fixed end cap 138 permit the passage of fluid through the column 104 while preventing the escape of particulate packing material from the column 104.

The frame 108 may be any structure configured for supporting the column 104 in a manner allowing the column 104 to be removed from the frame 108, and for supporting the compression flange 120. In the illustrated example, the frame 108 includes an upper column flange 142 abutting the column 104 at the first end 132, a lower column flange 144 abutting the column 104 at the second end 134, and one or more (typically two or more, and more typically four) struts 136 extending axially between the upper flange 142 and the lower flange 144. The struts 136 may be removably fastened to the upper flange 142 and to the lower flange 144 by any means, e.g., by utilizing bolts and nuts, etc. The struts 136 may be tightened against the upper flange 142 and the lower flange 144 such that the column 104 is clamped between the upper flange 142 and the lower flange 144. This design eliminates the need for any welding on the column 104 and hence simplifies the manufacturing and certification processes associated with pressurized vessels. The upper flange 142 has a bore aligned with the opening of the first end 132, and the lower flange 144 has a bore aligned with the opening of the second end 134. In the present example, the end cap 138 is removably mounted to the lower flange 144 at the bore by any means, e.g., by utilizing bolts and nuts, etc., although in other implementations may be removably mounted directly to the column 104 at the second end 134. In some implementations, the end cap 138 may be mounted so as to swing away from the bore or the second end 134. The frame 108 includes an additional set of struts 148 extending axially between the compression flange 120 and the upper column flange 142 so as to position the compression flange 120 at a fixed axial distance above the first column end 132. As described in more detail below, the compression flange 120 interfaces with a column packing station (not shown) to facilitate packing bed compression and to provide a plane of support or a base to which the movable piston head 112 can be locked, thereby facilitating detachment of the column module 100 from the packing station.

The column module 100 may further include running gear 152. In the illustrated example, the frame 108 includes a cart 156 attached to or integral with the lower column flange 144 and the running gear 152 is attached to the cart 156. The running gear 152 thus renders the entire column module 100 mobile along the floor or any other surface supporting the column module 100. The running gear 152 may be configured in any manner suitable for this purpose. As one example, the running gear 152 may include castor wheels or other type of wheels, or any other mechanism that facilitates movement along a surface. Moreover, the cart 156 provides sufficient space below the column 104 to facilitate unpacking and cleaning operations.

The locking mechanism 124 may be any device or mechanism configured for being movable (adjustable, actuatable, etc.) between an unlocked state (or position) in which the compression rod 116 and the piston head 112 are free to move axially in both directions (e.g., up or down), and a locked state (or position) in which the piston rod 116 and the piston head 112 are not free to move axially in both directions. The design of the locking mechanism 124 may depend on the size (inside diameter) of the column 104. In smaller versions, the locking mechanism 124 may be a mechanical locking mechanism as in the example shown in FIG. 1, while in larger versions the locking mechanism 124 may be assisted by hydraulics (e.g., include a hydraulic brake or rod clamp) as in the example shown in FIGS. 8-16. In some implementations, the locking mechanism 124 surrounds the piston rod 116 and is mounted to the compression flange 120. In the locked state, the locking mechanism 124 either engages the piston rod 116 or the piston head 112, either directly or indirectly, to prevent axial movement of both the piston rod 116 and the piston head 112. It will be noted that the piston head 112 is removably coupled to the piston rod 116 by any suitable coupling 162 so that a locking engagement with one affects the axial movement of both. The locking mechanism 124 may include a coupling and a fastener engaged with the coupling. In FIG. 1, the locking mechanism 124 includes a mechanical lock that includes a hollow threaded coupling 166, a first nut 168, a second nut 170 and one or more split spacers (not shown). The threaded coupling 166 extends through a bore of the compression flange 120 and the piston rod 116 in turn extends through the interior of the threaded coupling 166. The threaded coupling 166 floats with respect to the piston rod 116, and is held in place relative to the compression flange 120 as a result of the first nut 168 resting on the compression flange 120. The locked state of the locking mechanism 124 is described below.

Figure 2:
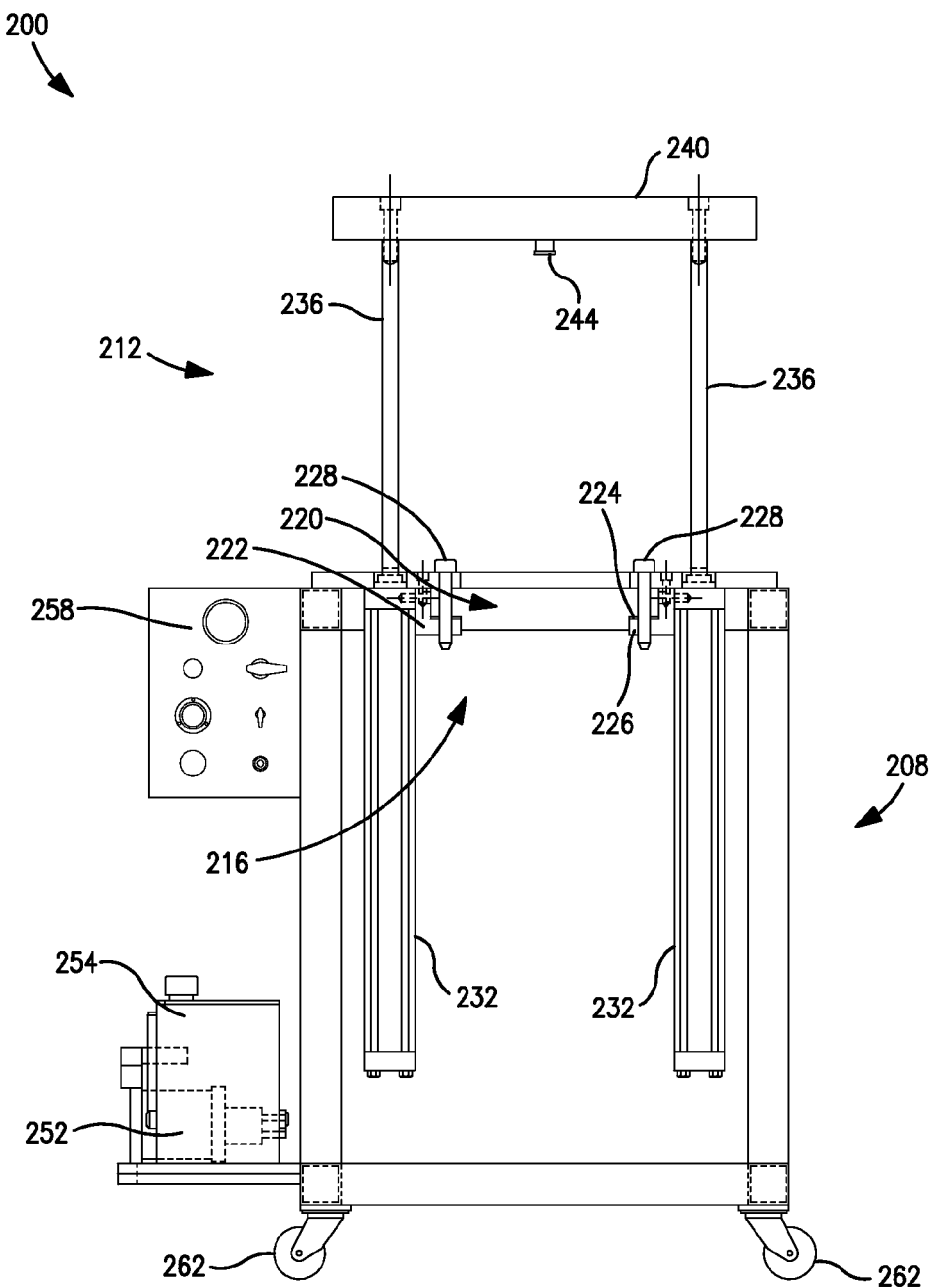
FIG. 2 is an elevation view of an example of a chromatography column packing module (or packing station) according to an implementation of the present disclosure.

FIG. 2 is an elevation view of an example of a chromatography column packing module (or packing station) 200 according to an implementation of the present disclosure. The packing module 200 generally includes a frame 208 and a hydraulic compression mechanism 212 supported by the frame 208. The packing module 200 further includes a mounting fixture 216 supported by or integral with the frame 208. The mounting fixture 216 includes a slot 220 positioned at an elevation sufficient to receive the compression flange 120 of the column module 100 illustrated in FIG. 1. The slot 220 may be defined by one or more mounting members 222 that present a landing 224 on which the compression flange 120 is supported. A wall of the mounting member(s) 222 defines an opening of lesser width than the slot 220. When mounted at the mounting fixture 216, the column module 100 extends through the opening. The mounting fixture 216 may include a securing device configured for securing the compression flange 120 once installed in the mounting fixture 216. In the illustrated example, the securing device includes one or more locking pins 228 inserted through respective holes of the mounting fixture 216 and corresponding holes of the compression flange 120. The slot 220 may be tapered relative to a horizontal plane and may include polymer glide strips (not shown) to facilitate the loading and positioning/alignment of the column module 100 and to reduce friction. The mounting fixture 216 may further include safety switches (not shown) that interface with the locking pins 228 to prevent unintended movement of the hydraulic compression mechanism 212.

The hydraulic compression mechanism 212 includes one or more hydraulic compression cylinders 232 supported by the frame 208, and corresponding hydraulic compression rods 236 that move axially in the hydraulic cylinders 232 between a fully raised (or extended) position and a fully lowered (or retracted) position. In the present example, two hydraulic cylinders 232 and corresponding compression rods 236 are provided and are laterally spaced from each other by a distance sufficient to accommodate installation of the column module 100. The two compression rods 236 are connected by a crossbeam 240. The crossbeam 240 includes a coupling 244 configured for coupling to the piston rod 116 of the column module 100. This configuration of the hydraulic compression mechanism 212 facilitates the use of smaller-diameter hydraulic cylinders 232 and compression rods 236, and results in a much lower overall height profile of the packing module 200 when in the lowered position. The hydraulic compression mechanism 212 may be associated with a hydraulic system that forms a part of the packing module 200. In the illustrated example the hydraulic system includes, in addition to the hydraulic compression mechanism 212, a pump 252 for pumping the hydraulic fluid and an associated reservoir 254 for the hydraulic fluid. Hydraulic fluid lines running between the pump 252 and the hydraulic cylinders 232 are not shown for simplicity. A control panel 258 may also be supported by the frame 208 and configured to allow the user to control the hydraulic operations of the packing module 200. In one example, the pump 252 is a pneumatic constant-pressure pump, which facilitates enabling the user to preselect the final packing pressure of the column 104 and maintain that pressure as long as the hydraulic system is energized.

The frame 208 of the packing module 200 may be any structure suitable for supporting the various components described above. In the present example, the frame 208 includes running gear 262 (e.g., wheels, etc.) to render the packing module 200 mobile. The mobility and reduced height of the packing module 200 are advantageous for the use and handling of such relatively large equipment within a laboratory or production environment where floor space and door sizes may be limiting.

Figure 3:
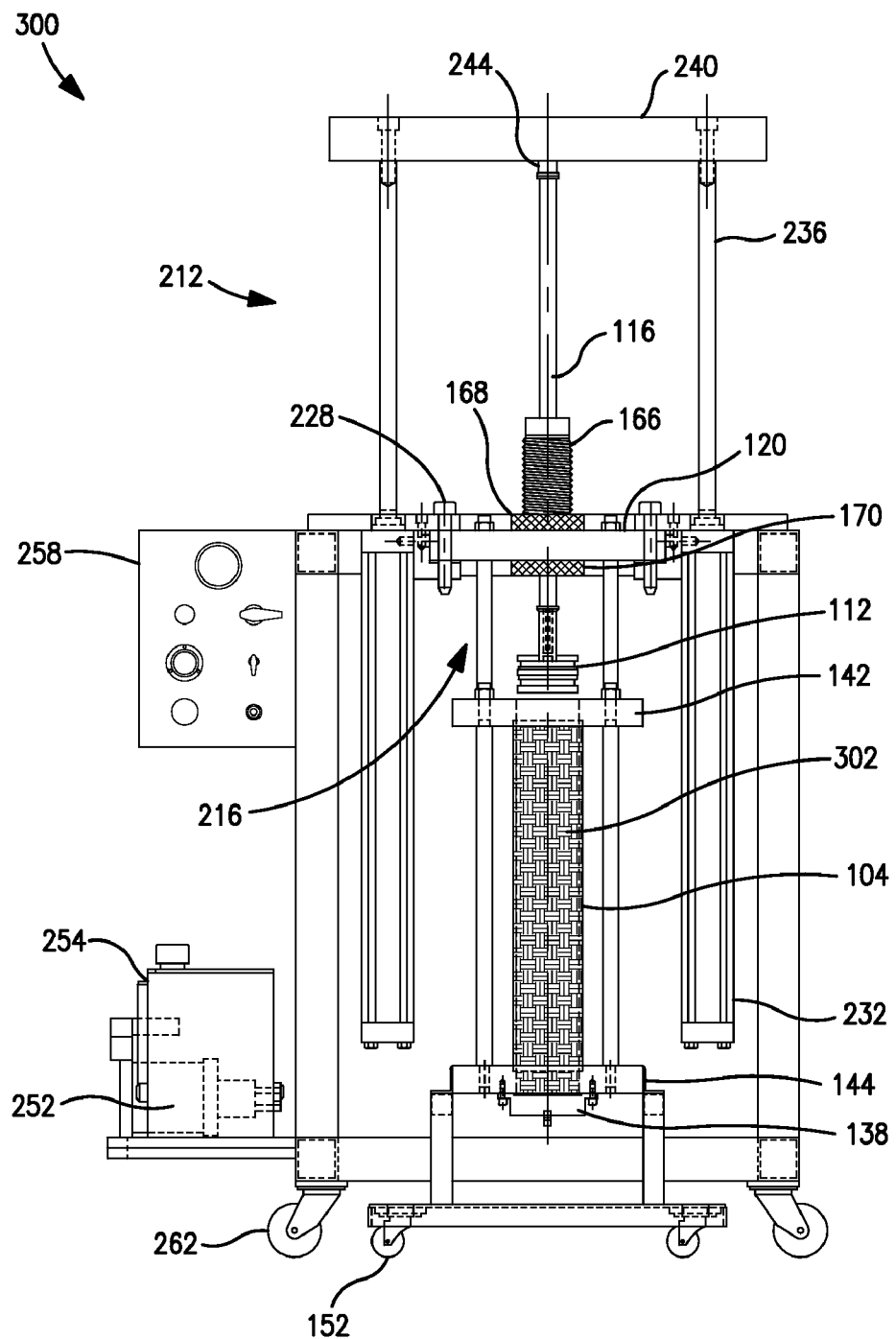
FIG. 3 is an elevation view of an example of a chromatographic packing (and unpacking) system, in which the column module illustrated in FIG. 1 has been installed in the packing module illustrated in FIG. 2.

FIG. 3 is an elevation view of a chromatographic packing (and unpacking) system 300, in which the column module 100 illustrated in FIG. 1 has been installed in the packing module 200 illustrated in FIG. 2. Before installing the column module 100, the hydraulic system of the packing module 200 is operated to raise the compression rods 236 and crossbeam 240 so as to accommodate the height of the piston rod 116 of the column module 100. The column module 100 is then docked to the packing module 200 by aligning the compression flange 120 of the column module 100 with the slot 220 of the mounting fixture 216 of the packing module 200, and then pushing the compression flange 120 into the slot 220. Mounting is completed when the locking pins 228 are inserted through the corresponding holes of the mounting fixture 216 and the compression flange 120. The piston rod 116 is then attached to the crossbeam 240 via the coupling 244. Prior to packing, the end cap 138 must also be attached so as to cover the second end 134 of the column 104 and retain the particulate packing material. An appropriate fluid line (not shown) is coupled to the outlet fitting of the end cap 138. As appreciated by persons skilled in the art, the particulate packing material is typically initially provided in a solvent as a slurry 302. Accordingly, the particulate packing material may be loaded into the column 104 by pouring or pumping the slurry 302 into the column 104 via the first end 132, with the piston head 112 removed. During filling of the column 104 with the slurry 302, the outlet line coupled to the end cap 138 is capped or valved off.

After filling, the piston head 112 is coupled to the piston rod 116. A fluid inlet line (not shown) is coupled to the fluid passage of the piston head 112, and at this time is vented or opened. The hydraulic system is then operated to drive the piston head 112 into the column 104 until all of the air in the column 104 is pushed out from the column 104 via the fluid passage of the piston head 112 and associated fluid inlet line. All air is evacuated when solvent begins to be displaced out from the inlet line, at which point the process is paused to cap or valve off the inlet line and vent the outlet line. The hydraulic system is then operated to resume driving the piston head 112 farther downward into the column 104 to compress the packing bed, during which time the solvent is displaced through the outlet line connected to the end cap 138. Compression continues until the desired packing pressure is achieved, as set and/or monitored by the user via the control panel 258.

Figure 4:
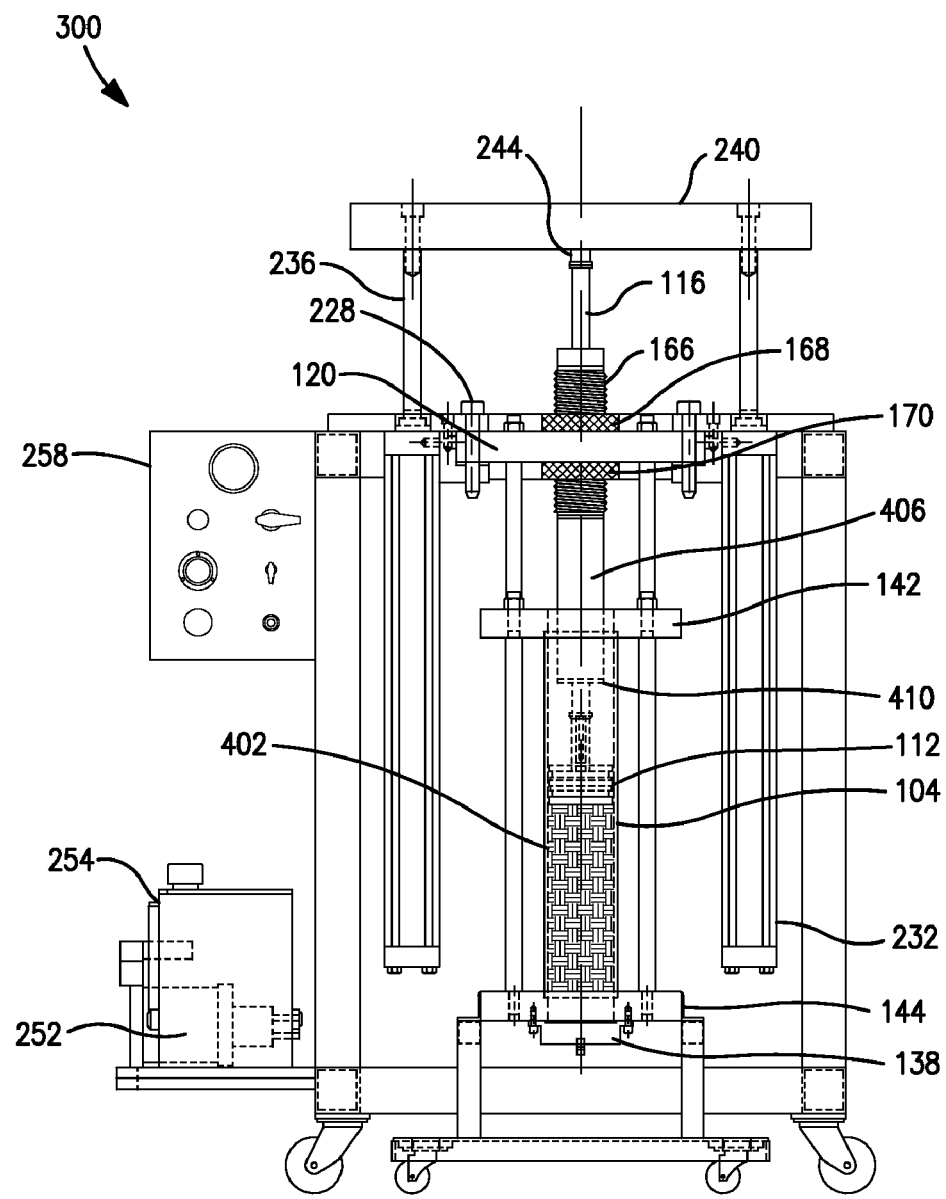
FIG. 4 is an elevation view of the packing system illustrated in FIG. 3 after the column has been packed to the desired pressure.

FIG. 4 is an elevation view of the packing system 300 after the column 104 has been packed to the desired pressure to form a particulate packing bed 402. Once the packing bed 402 is stabilized, the locking mechanism 124 is operated to lock the piston head 112 into the compression flange 120. This is done by placing one or more spacers 406 around the piston rod 116 as needed to span the axial distance between the lower end of the threaded coupling 166 and a plate 410 extending in a radial direction from the piston rod 116. The spacers 406 in this example are cylindrical clamshell-type structures having axial gaps to accommodate installing the spacers 406 around the piston rod 116. The first nut 168 and the second nut 170 are then tightened as needed to prevent upward movement of the threaded coupling 166. At this locked position, the piston rod 116 cannot be backed upward. The compressive forces from the packed bed 402 are transferred through the piston head 112, the rod 116, the plate 410, the spacer(s) 406, the second nut 170, the threaded coupling 166, and to the compression flange 120. With the piston head 112 locked in place in this manner, the hydraulic system may be operated to relieve the hydraulic pressure in the hydraulic system. Detachment entails decoupling the piston rod 116 from the crossbeam 240, raising the crossbeam 240, removing the locking pins 228 from the mounting fixture 216, and then sliding the column module 100 out from the mounting fixture 216. The column module 100 can then be easily and quickly detached from the packing module 200 and transported to any desired site of operation for its intended use as appreciated by persons skilled in the art (e.g., purification, reaction, synthesis). During detachment, transportation, and preparation for use at the site of operation, the piston head 112 remains locked in place and the column 104 consequently remains packed at the desired pressure.

Figure 5:
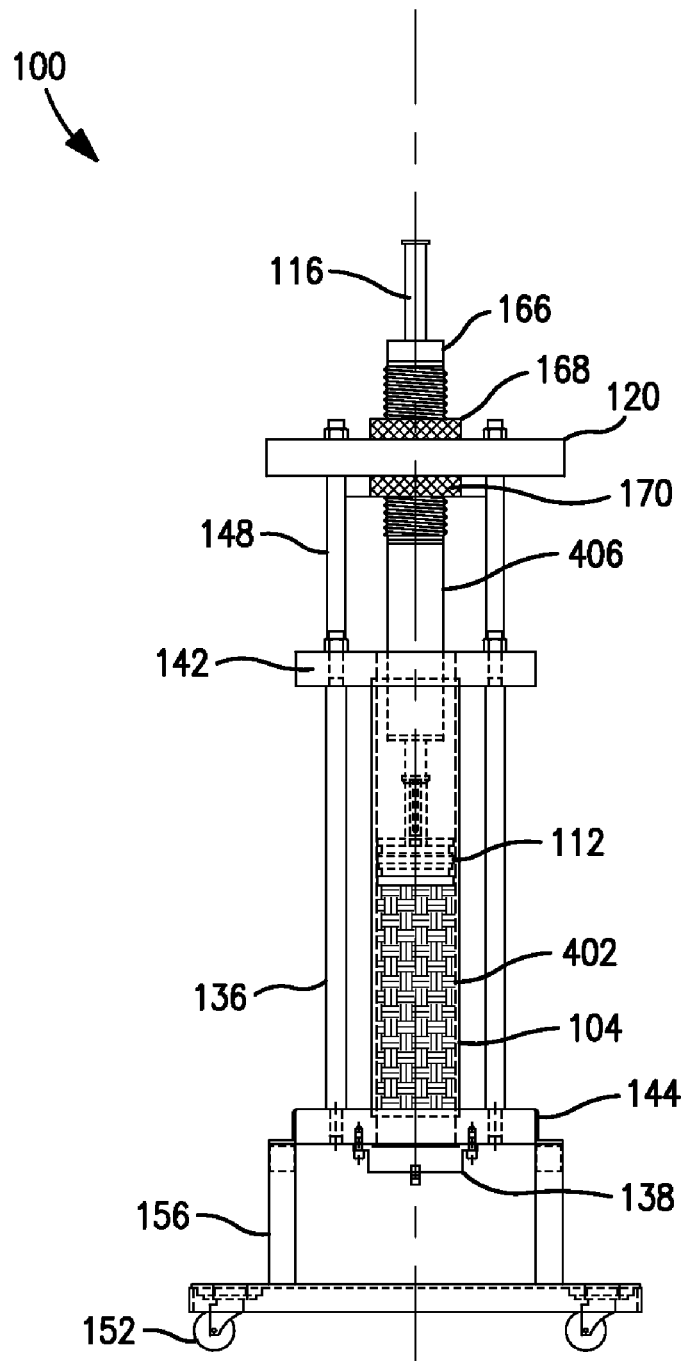
FIG. 5 is an elevation view of the column module illustrated in FIG. 3 with the column packed, and after removal from the packing module.

FIG. 5 is an elevation view of the column module 100 with the column 104 packed, and after removal from the packing module 200. It can be seen that none of the hydraulics or any other component of the packing module 200 need to remain with the column module 100 once the column 104 has been packed. Moreover, because the packed column module 100 is able to be removed from the packing module 200, the same packing module 200 may be utilized to sequentially pack any number of additional columns by repeating the steps described above for other column modules. In addition, the same packing module 200 may be utilized to pack other columns of various sizes, as well as columns of various lengths. As one example, the same packing module 200 may be compatible with 4-inch, 6-inch and 8-inch column diameters. The hydraulic system permits a wide range of packing pressures to be selected, and is able to compress any type of particulate packing material (sorbents, media, gels, resins, etc.) typically utilized in preparative-type columns.

Figure 6:
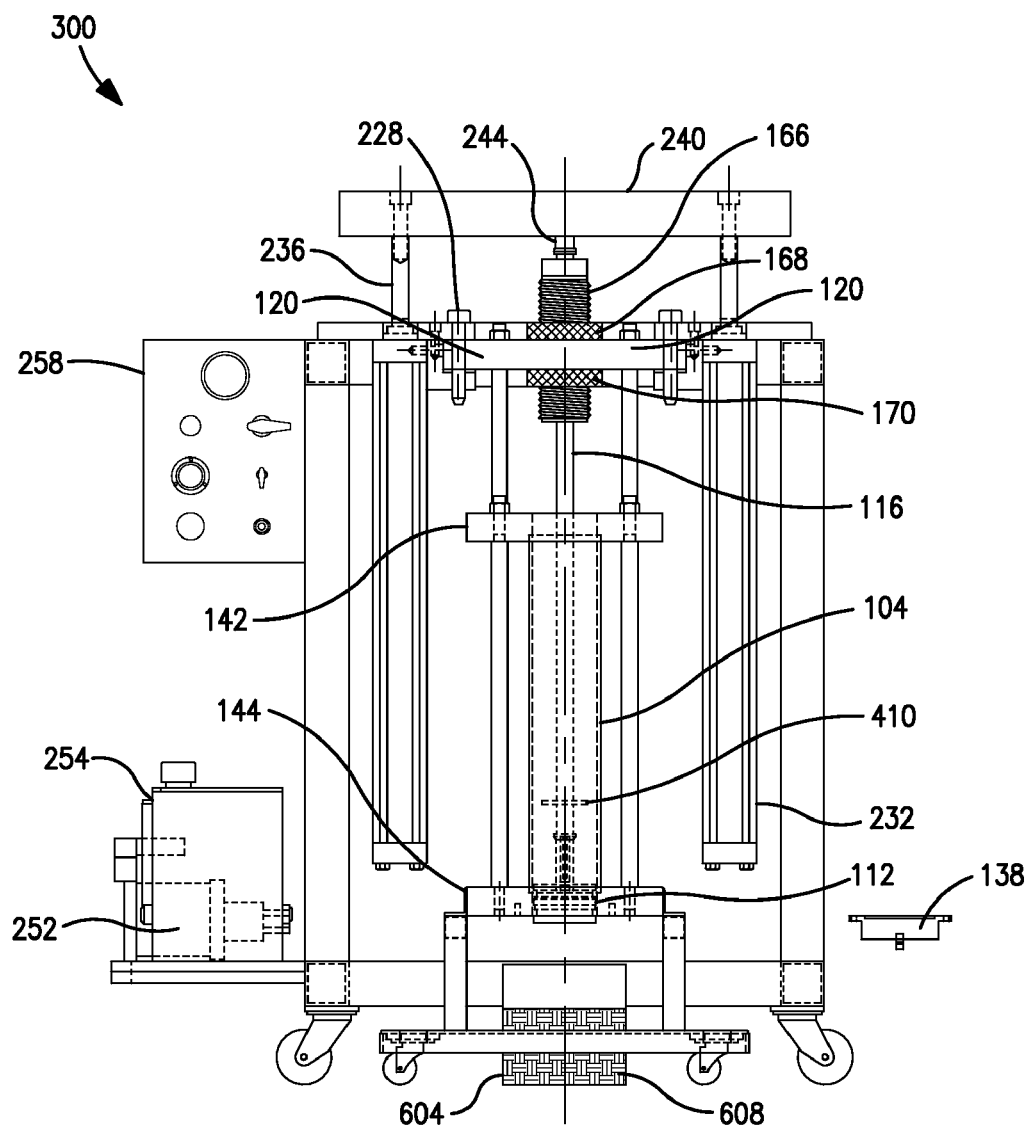
FIG. 6 is an elevation view of the packing system illustrated in FIG. 4 during unpacking of the column.

FIG. 6 is an elevation view of the packing system 300 during unpacking of the column 104. After the column 104 has been utilized at a site of operation, the same packing system 300 previously utilized to pack the column 104 may be utilized to unpack the column 104. The column module 100 is transported back to and re-docked with the packing module 200 in a manner similar to that described above in conjunction with preparation for the initial packing process. For unpacking, a receptacle 604 may be positioned underneath the second end 134 of the column 104, and the end cap 138 is then removed. The hydraulics system is then operated to advance the piston head 112 downward to push used packing material 608 through the column 104 and out from the second end 134 and into the receptacle 604. As the column 104 is being purged of the packing material 608, the compressive forces on the spacer(s) 406 (FIGS. 4 and 5) are removed, and hence the spacer(s) 406 may be removed from the compression rod 116.

Figure 7:
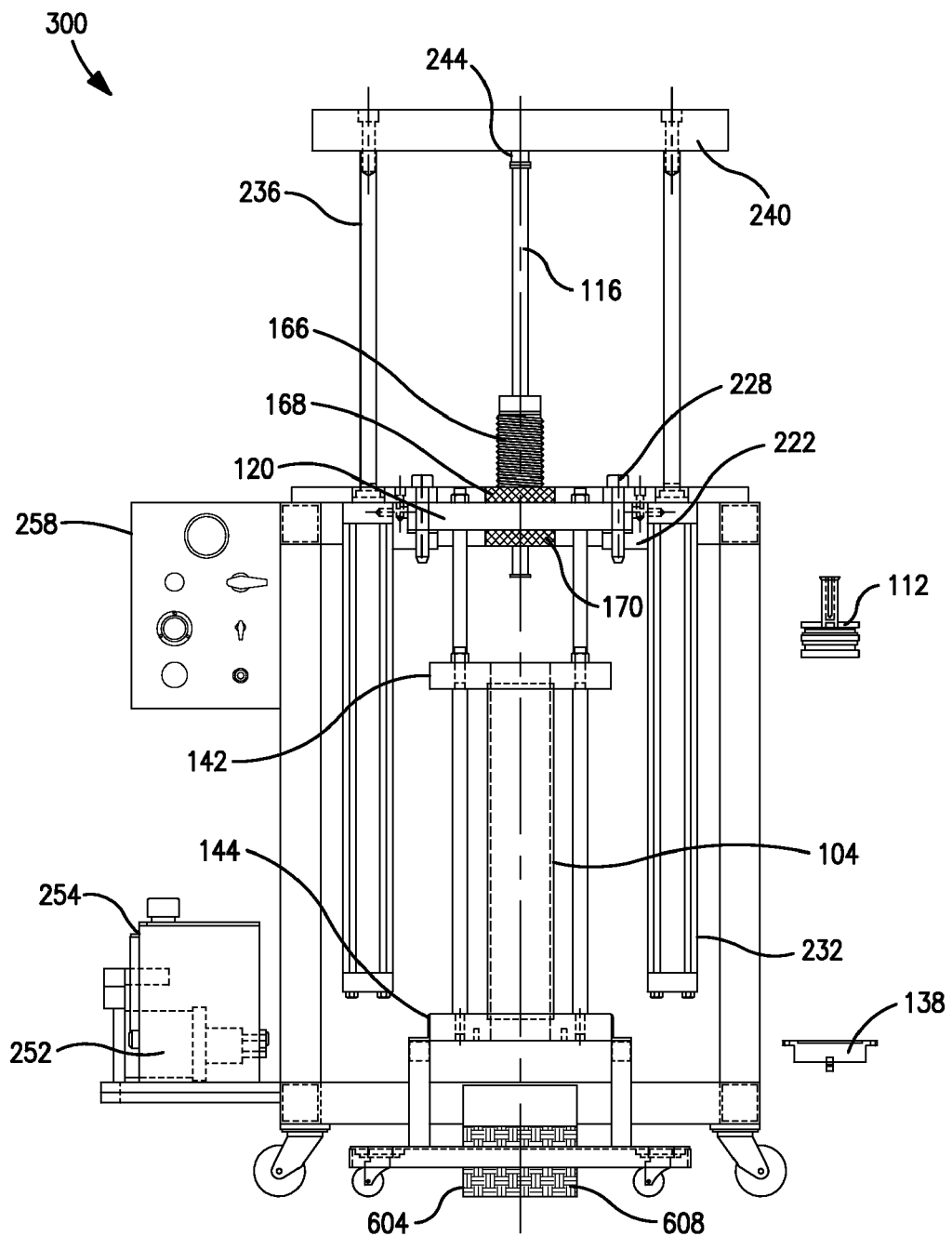
FIG. 7 is an elevation view of the packing system illustrated in FIG. 4 after unpacking of the column.

FIG. 7 is an elevation view of the packing system 300 after unpacking of the column 104. After the packing bed has been eliminated, the piston head 112 may be fully retracted out from the first end 132 of the column 104. At this time, the piston head 112 may be decoupled from the piston rod 116 and removed for cleaning. The column 104, end cap 138, and other components of the column module 100 may also be cleaned at this time.

FIGS. 8-16 illustrate an example of a column module and a packing module according to another embodiment. This embodiment is particularly useful in conjunction with large-diameter, large volume columns, which typically require the use of packing and handling equipment that likewise involve larger, heavier components. As size increases, the handling and ease of use of such columns, and related components such as end caps, locking mechanisms, etc., become even more of a consideration.

Figure 8:
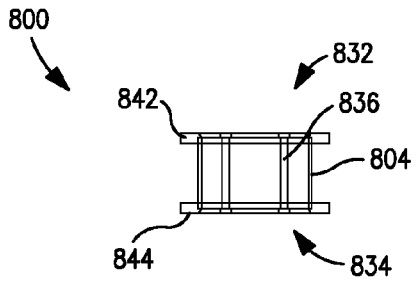
FIG. 8 is an elevation view of an example of a column assembly.

FIG. 8 is an elevation view of an example of a column assembly 800. The column assembly 800 includes a chromatography column 804, an upper flange 842 positioned at a first end 832 of the column 804, a lower flange 844 positioned at a second end 834 of the column 804, and a set of struts 836 axially extending between the upper flange 842 and the lower flange 844. The column 804 may have a large inside diameter. As typical examples, the inside diameter may range from 4-24 inches. It will be understood, however, that the inside diameter of the column 804 is not limited to this range and alternatively may be less than 4 inches or greater than 24 inches. As shown, the column 804 may have an aspect ratio such that its inside diameter is greater than its height.

Figure 9:
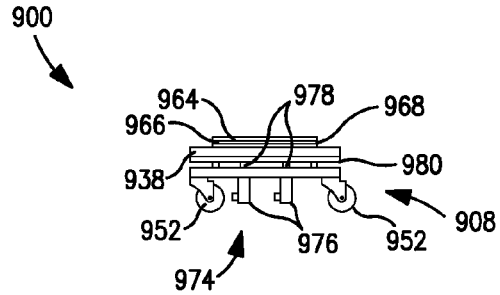
FIG. 9 is an elevation view of an example of an end cap assembly that may be utilized in conjunction with the column assembly illustrated in FIG. 8.

FIG. 9 is an elevation view of an example of an end cap assembly 900 that may be utilized in conjunction with the column assembly 800 illustrated in FIG. 8. The end cap assembly 900 includes an end cap 938. The end cap 938 may include a frit 964, a distribution plate 966, and a seal 968. As appreciated by persons skilled in the art, the distribution plate 966 is structured to facilitate collection of the liquid passing through the frit 964 and directing the liquid to an outlet port (not shown). The end cap assembly 900 may further include a frame 908 supporting the end cap 938. The frame 908 may include running gear 952 (e.g., wheels) to render the end cap assembly 900 a mobile unit. In the present example, the end cap assembly 900 further includes a hydraulic lifting mechanism 974 supported by the frame 908. The hydraulic lifting mechanism 974 is axially movable from a lowered position to a raised position relative to the frame 908. The hydraulic lifting mechanism 974 communicates with (or, stated differently, is mechanically referenced to) the end cap 938 such that the end cap 938 is axially movable with the hydraulic lifting mechanism 974. In the example specifically illustrated in FIG. 9, the hydraulic lifting mechanism 974 includes one or more hydraulic lifting cylinders 976 supported by the frame 908, and a corresponding number of hydraulic lifting rods 978 axially movable in the hydraulic lifting cylinders 976. The lifting rods 978 are attached to a base member 980 of the end cap 938. The hydraulic lifting mechanism 974 may communicate via hydraulic lines (not shown) with any suitable pump and associated hydraulic system, such as may be provided at a column packing station.

Figure 10:
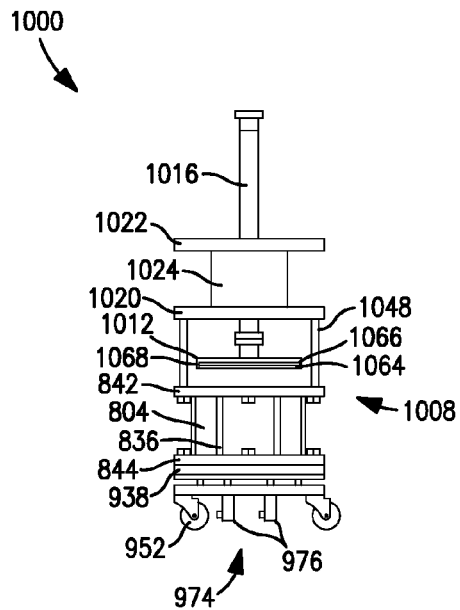
FIG. 10 is an elevation view of another example of a column module according to another implementation.

FIG. 10 is an elevation view of another example of a column module 1000 according to another implementation. The column module 1000 may be configured in particular for use with large columns 804 and associated end caps 938 such as respectively illustrated in FIGS. 8 and 9, but more generally may be utilized with any columns. The column module 1000 generally includes the end cap assembly 900, the column assembly 800 supported by the end cap assembly 900, a frame 1008, a piston (or compression) head 1012, a piston (or compression) rod 1016, a compression flange 1020 (or plate, etc.), and a locking mechanism 1024. The piston head 1012 may include a frit 1064, a distribution plate 1066, a seal 1068, and a fluid inlet passage (not shown) providing a fluid path from outside the piston head 1012 to the first end 832 of the column 804 via the distribution plate 1066 and the frit 1064, as appreciated by persons skilled in the art. The frame 1008 may be any structure suitable for supporting the column 804, the end cap 938, and the compression flange 1020. Hence, in the present example the frame 1008 may be considered as including the structural members associated with the end cap assembly 900 and the column assembly 800, described above and illustrated in FIGS. 8 and 9. The mobile portion of the end cap assembly 900 may be considered as a mobile frame supporting the main frame 1008 of the column module 1000, or as a mobile subframe or mobile frame portion that is part of the column module 1000 and removable therefrom. In addition, in the present example the frame 1008 includes an additional set of struts 1048 axially extending between the upper flange 842 of the column assembly 800 and the compression flange 1020, whereby the compression flange 1020 is fixed at an axial distance from the first end 832 of the column 804. The compression flange 1020 may be utilized as a mounting flange that docks with a packing module. Alternatively, an additional mounting flange 1022 may be provided for this purpose and located at a higher elevation than the compression flange 1020.

The locking mechanism 1024 may be mounted on the compression flange 1020. In implementations in which the additional mounting flange 1022 is provided, the locking mechanism 1024 may be mounted between the compression flange 1020 and the mounting flange 1022. The mounting flange 1022 may be supported by the locking mechanism 1024 or by some portion (not shown) of the frame 1008. In the present example, the locking mechanism 1024 includes a hydraulic lock or clamp configured to be actuated by hydraulics from an unlocked position to a locked position at which the hydraulic lock engages the piston rod 1016 so as to prevent axial movement of the piston rod 1016 and the piston head 1012 coupled thereto. The hydraulic locking mechanism 1024 may be considered more appropriate for handling the larger, heavier components associated with larger columns 804, as compared to a mechanical locking mechanism. The hydraulic locking mechanism 1024 may communicate via hydraulic lines (not shown) with any suitable pump and associated hydraulic system, such as may be provided at a column packing station.

Figure 11:
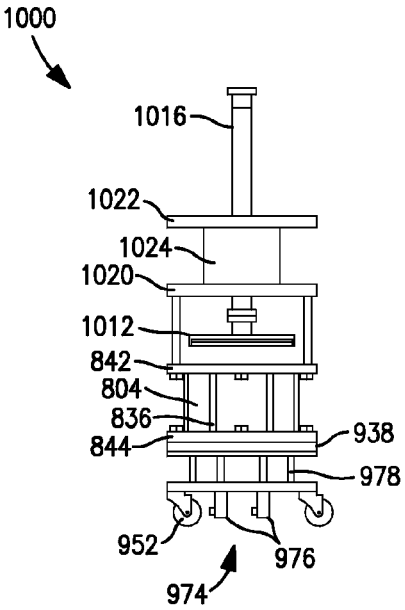
FIG. 11 is an elevation view of the column module illustrated in FIG. 10, but in a raised position.

In FIG. 10, the column module 1000 is in a lowered position. That is, the hydraulic lifting mechanism 974 that supports the various components of the column module 1000 is in a lowered position. FIG. 11 is an elevation view of the column module 1000 illustrated in FIG. 10, but in a raised position. That is, the hydraulic lifting mechanism 974 has been actuated so as to raise the various components of the column module 1000 relative to the frame 908 supporting the hydraulic lifting cylinders 976.

Figure 12:
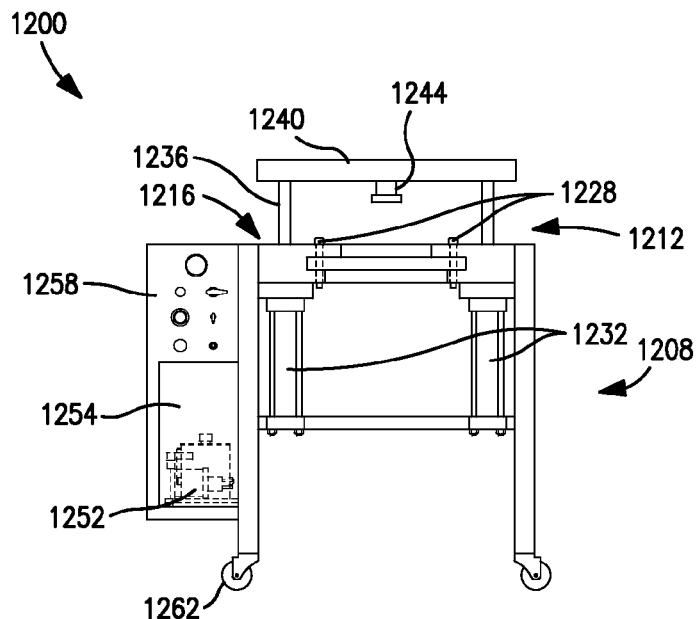
FIG. 12 is an elevation view of another example of a chromatography column packing module (or packing station).

FIG. 12 is an elevation view of another example of a chromatography column packing module (or packing station) 1200. The packing module 1200 may be generally similar to that illustrated in FIG. 2 and described above, and modified as necessary to support larger, heavier components. Accordingly, the packing module 1200 in the present example includes a frame 1208 and a hydraulic compression mechanism 1212 supported by the frame 1208. The packing module 1200 further includes a slotted mounting fixture 1216 supported by or integral with the frame 1208 with one or more locking pins 1228 and optionally other types of securing or safety devices. The hydraulic compression mechanism 1212 includes one or more hydraulic cylinders 1232 supported by the frame 1208, and corresponding compression rods 1236 that move axially in the hydraulic cylinders 1232 between a fully raised (or extended) position and a fully lowered (or retracted) position. In the present example, two hydraulic cylinders 1232 and corresponding compression rods 1236 are provided and are connected by a crossbeam 1240. The crossbeam 1240 includes a coupling 1244 configured for coupling to the piston rod 1016 of the column module 1000. The hydraulic compression mechanism 1212 may be associated with a hydraulic system that forms a part of the packing module 1200. In the illustrated example the hydraulic system includes, in addition to the hydraulic compression mechanism 1212, a pump 1252, a hydraulic fluid reservoir 1254, associated hydraulic fluid lines (not shown), and a control panel 1258. The hydraulic system may be utilized to power the hydraulic lifting mechanism 974 and the hydraulic locking mechanism 1024 of the column module 1000 (FIG. 10) when docked to the packing module 1200. The frame 1208 of the packing module 1200 may be any structure suitable for supporting the various components of the packing module 1200. In the present example, the 1208 frame includes running gear 1262 (e.g., wheels) to render the packing module 1200 mobile.

Figure 13:
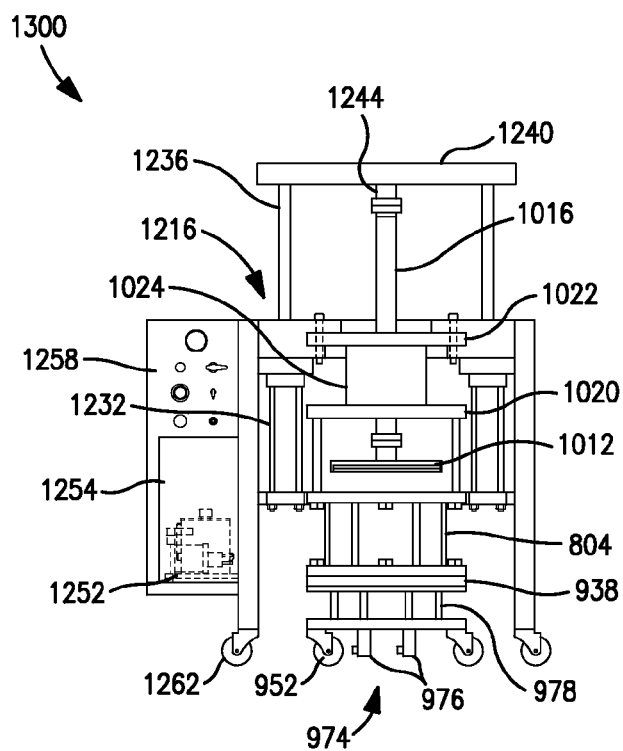
FIG. 13 is an elevation view of another example of a chromatographic packing (and unpacking) system, in which the column module illustrated in FIGS. 10 and 11 has been installed in the packing module illustrated in FIG. 12.

FIG. 13 is an elevation view of another example of a chromatographic packing (and unpacking) system 1300, in which the column module 1000 illustrated in FIGS. 10 and 11 has been installed in the packing module 1200 illustrated in FIG. 12. The packing system 1300 may be operated in a manner similar to that illustrated in FIG. 3. In the present example, the mounting flange 1022 is provided with the column module 1000 and is utilized to dock the column module 1000 to the packing module 1200. For this purpose, the hydraulic lifting mechanism 974 is first actuated to raise the column module 1000 such that the mounting flange 1022 may be aligned with the mounting fixture 1216 of the packing module 1200. The column module 1000 is then slid into the packing module 1200, the mounting flange 1022 is secured in the mounting fixture 1216, and the piston rod 1016 is coupled to the crossbeam 1240. The column 804 may then be packed or unpacked in a manner generally similar to the descriptions provided earlier in this disclosure.

Figure 14:
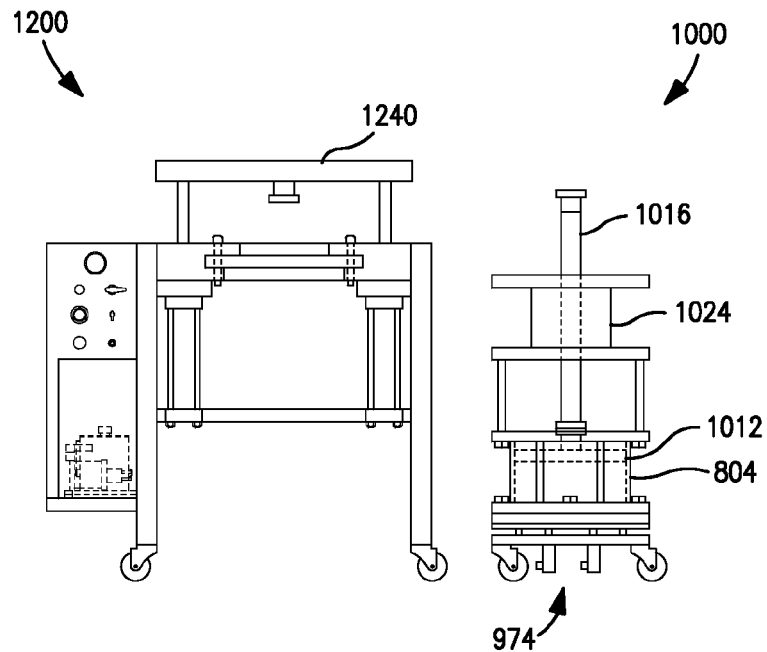
FIG. 14 is an elevation view of the column module illustrated in FIGS. 10 and 11 and the packing module illustrated in FIG. 12, after the column has been packed and the column module has been removed from the packing module.

FIG. 14 is an elevation view of the column module 1000 illustrated in FIGS. 10 and 11 and the packing module 1200 illustrated in FIG. 12, after the column 804 has been packed and the column module 1000 has been removed from the packing module 1200. After packing the column 804 to a desired pressure, the packing module 1200 is in the lowered position as shown in FIG. 14. The hydraulic locking mechanism 1024 is then actuated to lock the piston head 1012 in place, and the piston rod 1016 is then decoupled from the crossbeam 1240. The entire column module 1000 may then be removed from the packing module 1200 and transported as a single unit to a site of operation. To facilitate handling and transport, the column module 1000 may be moved to the lowered position by the hydraulic lifting mechanism 974 after removal from the packing module 1200, as shown in FIG. 14.

Figure 15:
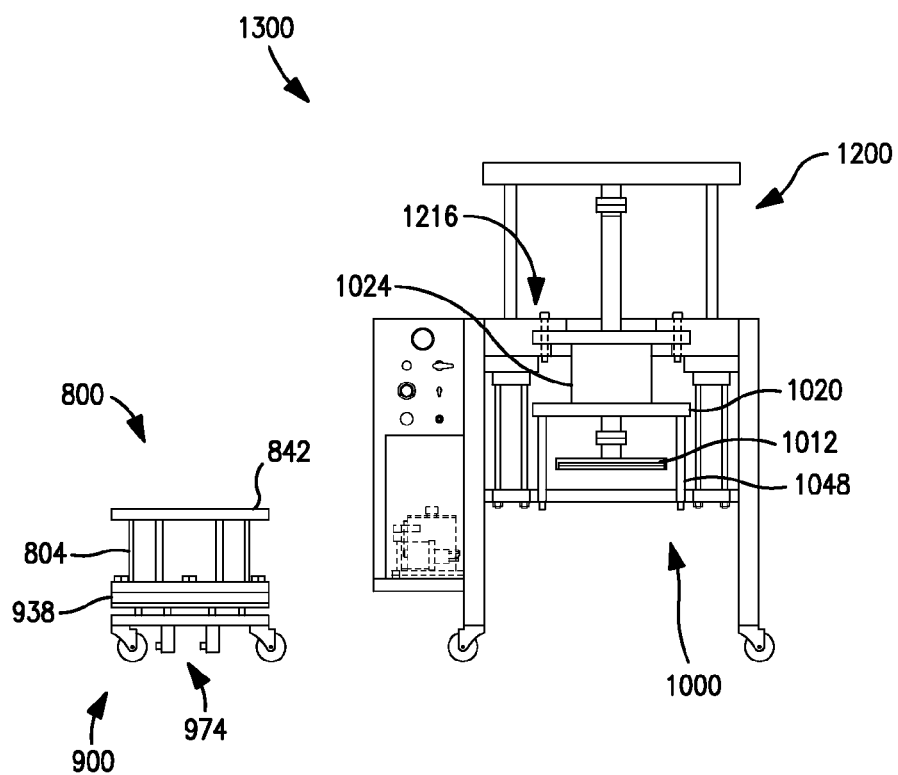
FIG. 15 is an elevation view of the packing system illustrated in FIG. 13, with the column assembly and the end cap assembly removed from the packing system as a single unit.

FIG. 15 is an elevation view of the packing system 1300 illustrated in FIG. 13, with the column assembly 800 and the end cap assembly 900 removed from the packing system 1300 as a single unit. In this example, the packing system 1300 has been operated to unpack the column 804 while the hydraulic locking mechanism 1024 is in the unlocked state, and the packing module 1200 has been raised to the raised position to remove the piston head 1012 from the unpacked column 804. With the column module 1000 still being supported by the mounting fixture 1216 of the packing module 1200, the column assembly 800 is detached from the column module 1000, such as by decoupling (or unfastening, etc.) the upper flange 842 of the column assembly 800 from the struts 1048 attached to the compression flange 1020. The hydraulic lifting mechanism 974 may then be operated to lower the column assembly 800 and the end cap assembly 900, at which point the column assembly 800 and the end cap assembly 900 may be removed from the packing system 1300 as an integrated unit. This configuration enables the column 804 and the end cap 938 to be cleaned or otherwise handled separately from the remaining portions of the column module 1000 while the remaining portions remain attached to the packing module 1200.

Figure 16:
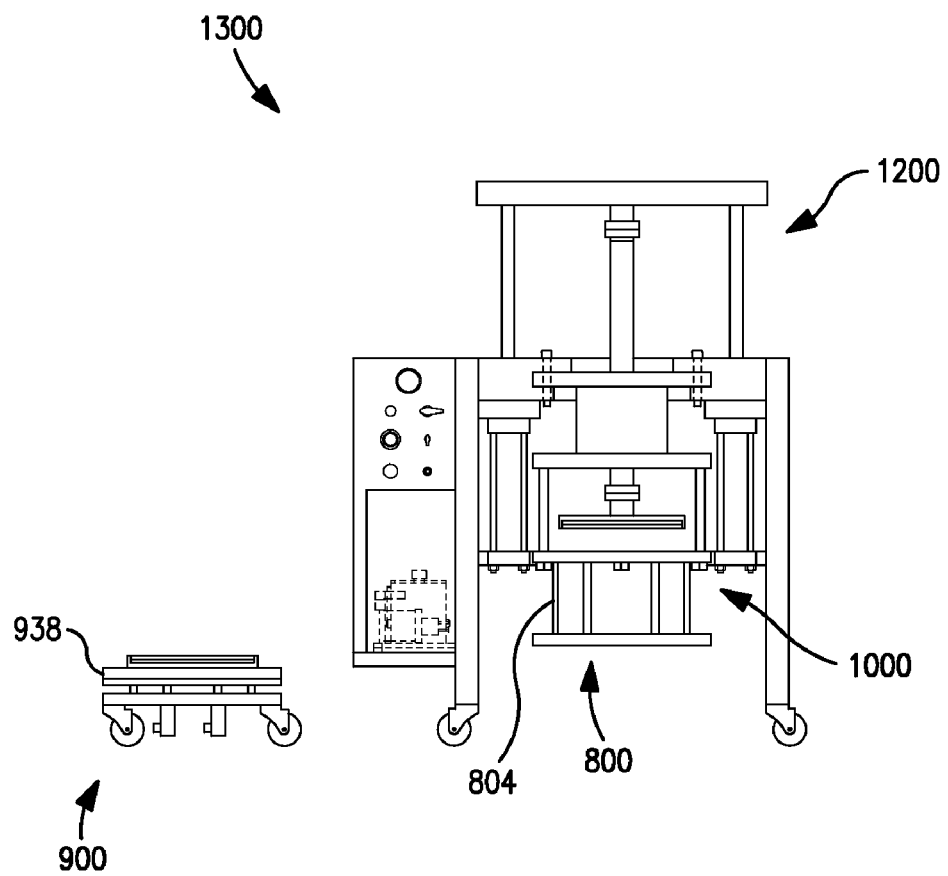
FIG. 16 is an elevation view of the packing system illustrated in FIG. 13, with the end cap assembly removed from the packing system as a single unit.

FIG. 16 is an elevation view of the packing system 1300 illustrated in FIG. 13, with the end cap assembly 900 removed from the packing system 1300 as a single unit. This configuration is similar to that illustrated in FIG. 15, except that the column assembly 800 remains loaded in the column module 1000. After unpacking the column 804, the end cap assembly 900 is detached from the column assembly 800, such as by decoupling (or unfastening, etc.) the end cap 938 from the lower flange 844 of the column assembly 800. The hydraulic lifting mechanism 974 may then be operated to lower the end cap assembly 900, at which point the end cap assembly 900 may be removed from the packing system 1300 as a single unit. This configuration enables the end cap 938 and other components of the end cap assembly 900 to be cleaned or otherwise handled separately from the remaining portions of the column module 1000 while the remaining portions remain attached to the packing module 1200. The end cap 938 may also be separated from the column assembly 800 in this manner in preparation for unpacking the column 804.

An advantage of implementations taught herein is the ability to pack a chromatography column, lock the piston in place and then remove the column from the packing station for use at a site of operation (e.g., purification, reaction, synthesis, etc.) that may be remote from the packing station. This reduces the footprint and weight of the column-containing apparatus that is actually to be utilized at the site of operation, while also isolating the separation process from any contaminates associated with the packing process, e.g. hydraulic fluid, resin, etc. In the implementation illustrated in FIGS. 8-16, the additional hydraulics simplify the handling of larger, heavier components and ease the operation of the column module and the packing module. In addition, the integral lifting cart facilitates the removal of the end cap and the column for purposes of unpacking, cleaning, etc.

While the examples provided above have focused on the use of the type of columns typically characterized as preparative columns, no limitation is placed on the type of column that may be utilized in the implementations taught herein. As an example, the column may be an analytical column. In particular, a large-diameter analytical column may benefit from the implementation of one or more of the aspects described in this disclosure, including the utilization of hydraulically assisted components and piston-locking features.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A column module for a chromatographic packing system, the column module comprising:
   a frame;
   a column removably supported by the frame and comprising a first end and an axially opposing second end;
   a piston head axially movable in the column and removable from the column;
   a flange attached to the frame in a fixed position at an axial distance from the first end;

a piston rod extending through a bore of the flange and removably coupled to the piston head;

a locking mechanism movable from an unlocked state in which the piston rod and the piston head are axially movable relative to the column, to a locked state in which the locking mechanism prevents the piston rod and the piston head from axially moving away from the column, wherein the frame, the column, the piston head, the flange, the piston rod and the locking mechanism are movable as a unit while in the locked state; and an end cap assembly comprising a hydraulic lifting mechanism and an end cap supported by the hydraulic lifting mechanism, wherein:

the end cap assembly is attached to the frame wherein the end cap communicates with the column at the second end;

the end cap assembly is removable from the frame wherein the end cap assembly, including the end cap and the hydraulic lifting mechanism, is removable as a single unit;

the column when removed from the frame is removable as a single unit with the end cap assembly and the hydraulic lifting mechanism; and the hydraulic lifting mechanism is axially movable from a lowered position to a raised position while the locking mechanism is in the unlocked state and in the locked state, wherein the end cap is axially movable with the hydraulic lifting mechanism and, while the end cap assembly is attached to the frame, the column and the flange are axially movable with the hydraulic lifting mechanism.

2. The column module of claim 1, wherein the locking mechanism comprises a coupling and a fastener engaging the coupling.

3. The column module of claim 2, wherein the coupling is threaded and the fastener comprises a first nut threaded to the coupling on a first side of the flange and a second nut threaded to the coupling on a second side of the flange.

4. The column module of claim 1, further comprising a spacer removably interposed between the locking mechanism and a plate extending from the piston rod.

5. The column module of claim 1, wherein the locking mechanism comprises a clamping mechanism removably engaging the piston rod.

6. The column module of claim 5, wherein the clamping mechanism is hydraulically actuated.

7. A chromatographic packing system comprising the column module of claim 1, wherein the frame supporting the column is a first frame, and further comprising:

a second frame comprising a mounting fixture; and a hydraulic compression mechanism supported by the second frame and comprising a coupling axially movable from a raised position to a lowered position, and wherein:

the flange is removably engaged with the mounting fixture;

the piston rod is removably coupled to the coupling, wherein the piston rod and the piston head are axially movable with the coupling; and the column module is removably mounted as a unit to the second frame via the engagement of the flange with the mounting fixture.

8. The chromatographic packing system of claim 7, wherein the hydraulic compression mechanism comprises a first cylinder and a second cylinder located at either side of the column, a first compression rod and a second compression rod respectively movable in the first cylinder and the second cylinder, and a crossbeam adjoining the first compression rod the second compression rod, and wherein the coupling is located at the crossbeam.

9. The chromatographic packing system of claim 7, wherein the first frame includes a mobile frame portion supporting the column and the hydraulic lifting mechanism, and the column and the hydraulic lifting mechanism are removable as a single unit from the first frame.

10. The chromatographic packing system of claim 7, further comprising an end cap removably located at the second end and comprising a frit, wherein the end cap is axially movable with the hydraulic lifting mechanism.

11. The chromatographic packing system of claim 10, wherein the first frame includes a mobile frame portion supporting the end cap and the hydraulic lifting mechanism, and the end cap and the hydraulic lifting mechanism are removable as a single unit from the first frame.

12. The column module of claim 1, wherein the locking mechanism is mounted to the flange, and in the unlocked state the piston rod and the piston head are axially movable relative to the flange.

13. The column module of claim 1, wherein at the locked state, the locking mechanism engages at least one of the piston rod and the piston head.

14. The column module of claim 1, wherein the end cap assembly comprises running gear configured for assisting removal of the end cap assembly from the frame.

* * * * *

UNITED STATES PATENT AND TRADEMARK OFFICE
CERTIFICATE OF CORRECTION

PATENT NO. : 8,066,876 B2 Page 1 of 1
APPLICATION NO. : 12/623771
DATED : November 29, 2011
INVENTOR(S) : Thomas Wesley Hampton et al.

It is certified that error appears in the above-identified patent and that said Letters Patent is hereby corrected as shown below:

On the face page, in field (75), in "Inventors", in column 1, line 3, delete "(DE)" and insert -- (GB) --, therefor.

In column 14, line 20, in Claim 8, delete "rod" and insert -- rod, --, therefor.

Signed and Sealed this
Tenth Day of January, 2012

David J. Kappos
*Director of the United States Patent and Trademark Office*